(12) United States Patent
Yamada (10) Patent No.: US 10,299,829 B2
(45) Date of Patent: May 28, 2019

(54) TISSUE REPAIR SYSTEM

(71) Applicant: Ronald Yamada, Orangevale, CA (US)

(72) Inventor: Ronald Yamada, Orangevale, CA (US)

(73) Assignee: Ronald Yamada, Manteca, CA (US)

( * ) Notice: Subject to any disclaimer, the term of this patent is extended or adjusted under 35 U.S.C. 154(b) by 173 days.

(21) Appl. No.: 15/345,063

(22) Filed: Nov. 7, 2016

(65) Prior Publication Data

US 2018/0125531 A1 May 10, 2018

(51) Int. Cl.
*A61B 17/04* (2006.01)
*A61B 17/34* (2006.01)
*A61B 17/12* (2006.01)
*A61B 17/068* (2006.01)
*A61B 17/06* (2006.01)
*A61B 17/064* (2006.01)
*A61B 17/22* (2006.01)

(52) U.S. Cl.
CPC ...... *A61B 17/3468* (2013.01); *A61B 17/0482* (2013.01); *A61B 17/068* (2013.01); *A61B 17/12* (2013.01); *A61B 17/3403* (2013.01); *A61B 2017/061* (2013.01); *A61B 2017/0646* (2013.01); *A61B 2017/0647* (2013.01); *A61B 2017/06095* (2013.01); *A61B 2017/22044* (2013.01); *A61B 2017/3409* (2013.01)

(58) Field of Classification Search
CPC ........... A61F 2/0811; A61F 2002/0882; A61B 17/0401; A61B 2017/0409; A61B 17/0469; A61B 2017/0417; A61B 2017/0464

USPC ....... 606/232, 139, 213, 300, 144, 228, 145, 606/148
See application file for complete search history.

(56) References Cited

U.S. PATENT DOCUMENTS

| | | |
|---|---|---|
| 5,059,206 A | 10/1991 | Winters |
| 5,500,000 A | 3/1996 | Feagin et al. |
| 6,306,159 B1 | 10/2001 | Schwartz et al. |
| 6,551,343 B1 | 4/2003 | Törmälä et al. |
| 7,608,092 B1 | 10/2009 | Schaffhausen |
| 7,871,440 B2 | 1/2011 | Schwartz et al. |
| 8,006,700 B2 | 8/2011 | Demopulos |
| 2002/0019649 A1 | 2/2002 | Sikora et al. |
| 2005/0033363 A1* | 2/2005 | Bojarski ............ A61B 17/0401 606/228 |
| 2006/0178680 A1 | 8/2006 | Nelson et al. |
| 2010/0010049 A1 | 1/2010 | Goble et al. |
| 2010/0010497 A1 | 1/2010 | Goble et al. |
| 2010/0249835 A1 | 9/2010 | Schwartz et al. |
| 2011/0022084 A1 | 1/2011 | Sengun et al. |
| 2011/0118757 A1* | 5/2011 | Pierce ................ A61B 17/0482 606/144 |

(Continued)

OTHER PUBLICATIONS

International Search Report issued by ISA/US for International Application No. PCT/US2017/015642 dated Apr. 7, 2018, pp. 1-2.

(Continued)

*Primary Examiner* — Julie A Szpira
(74) *Attorney, Agent, or Firm* — Haynes and Boone, LLP (57) ABSTRACT

An apparatus for repairing an anatomical tear, such as a tear in the meniscus of a human knee. The apparatus includes a guide cannula directing a penetrating shaft through the meniscal tear and through the outer skin layer of the knee. The penetrating shaft pulls a line to the outside of the skin layer of the knee where it is used to pull or kedge a repair implant into position across the meniscal tear.

19 Claims, 7 Drawing Sheets

(56) References Cited

U.S. PATENT DOCUMENTS

2014/0135835 A1   5/2014   Stone et al.

OTHER PUBLICATIONS

Written Opinion of the International Searching Authority issued by ISA/US for International Application No. PCT/US2017/015642 dated Apr. 7, 2018, pp. 1-5.

* cited by examiner

PRIOR ART

TISSUE REPAIR SYSTEM

BACKGROUND OF THE INVENTION

The present invention relates to a novel and useful apparatus or system for repairing a tear in an anatomical structure such as soft and connective tissue. For example, a meniscus tear may be the subject of use of the apparatus of the present application in the human knee.

A meniscus tear is a common injury caused by forceful twisting of the knee, usually during participation in vigorous or sports activities. Each knee of a human anatomy includes a pair of menisci. Each meniscus is a rubbery C-shaped disc that cushions the knee and provides steadiness during ambulatory motion.

Surgery is often performed to repair tears in a meniscus by the use of implants such as darts, anchors, sutures and other devices. Such surgery is desirable to maintain meniscal cushioning and stability of the knee joint and prevent premature arthritis.

Repair of a tear in a meniscus can be performed sing various techniques, such as open, arthroscopic with external incisions, or solely arthroscopic procedures. The open technique accesses a tear in a meniscus through large outside incisions. An arthroscopic with external incisions technique uses an arthroscope to visualize a tear while outside incisions are used to complete the repair. Both techniques requiring outside incisions increase the risk of injury to vulnerable tissues.

In contrast, an all-inside technique places arthroscope and instruments solely within the joint and accomplishes repair without larger outside incisions. Such inside technique is preferred because it avoids risks associated with the larger outside incisions. However, instruments of the prior art limit a successful all-inside technique repair to a narrow range of tears.

Optimal meniscal repair requires correct placement of an implant perpendicular to the long axis of a tear. To achieve an optimal all-inside repair, an instrument must be able to 1) access the tear, 2) align properly with the tear, 3) minimize any deforming force at the tear by insertion of an implant in optimal alignment, and 4) insert an implant at optimal depth.

All-inside instruments of the prior art generally hold or house the repair implant within a distal portion or tip of a delivery cannula for deployment. However, a repair implant, in certain cases, may be initially held by a delivery cannula apart from the distal portion or tip, e.g. at the mid-portion, and then advanced to the tip for deployment. These prior art all-inside instruments are pushed or utilize a pushing force to deliver a repair implant at a tear site. Pushing a straight instrument aligned perpendicularly to the long axis of a tear minimizes a lateral shear force at the tear. Pushing an instrument obliquely to the optimal perpendicular angle of insertion generates a deforming lateral shear force at the tear site and produces a buckled, deformed, and weak repair. Moreover, prior art instruments can be utilized in only a limited area (posterior) of a meniscus because anatomic constraints prevent optimal alignment of instrument with a tear.

Certain all-inside instruments of the prior art have an angulated distal portion or tip to improve alignment with a tear in a meniscus. With this angulation, the axis of the angulated tip diverges from axis of the proximal portion or handle of the push operated instrument. However, when such handle is 'pushed' to advance instrument at a tear site, the distal tip advances along the axis of instrument handle and not along the axis of the angulated distal tip. Since the axis of the handle diverges from correct direction of insertion, a lateral shear force is generated at the tear as the implant is 'pushed' across tear, again creating a deformed and weak repair.

In addition, a practitioner pushing an instrument of the prior art can misperceive resistance during insertion of the instrument tip. As a result, an implant may be inserted at an improper depth. Over penetration of an implant risks damage to adjacent structures, while under penetration risks poor fixation and weakened repair.

In the past, systems have been proposed to repair tissue such as meniscus tears. For example, U.S. Pat. Nos. 5,059,206, 5,500,000, 6,551,343, and US Patent Publication 2010/0010497 show systems for inserting meniscus repair devices in which a dart-like member is passed across a meniscus tear and left in place as an implant.

U.S. Pat. Nos. 6,306,159, 7,608,092, 8,006,700, and US Patent Publication 2002/0019649 describe meniscus repair devices using anchors that are inserted by pushing across a meniscal tear and securing the anchors by way of sutures or the like.

United States Patent Publication 2010/0249835 teaches a medical device for repairing tissue in which a conduit is provided to facilitate transfer of blood from a vascular region of tissue to a damaged tear. The conduit is secured by filaments that are positioned adjacent the tear walls.

U.S. Pat. No. 7,871,440 describes a unitary surgical device in which two groups of devices are shown in the form of anchors or a matrix material. The two devices are delivered from a base that is pushed into the vicinity of the tissue, such as a meniscus.

An apparatus which is capable of repairing tears without buckling, such as meniscal tears of various types, would be a notable advance in the medical field.

SUMMARY OF THE INVENTION

In accordance with the present application, a novel and useful tissue repair apparatus is herein provided.

The apparatus of the present application utilizes a guide. The guide may take the form of a conventional guide cannula and include a handle at one end. Also, the guide cannula may be formed with a relatively straight shaft or an angulated shaft in order to reach meniscus tears that are difficult to approach due to anatomical structures in the knee.

A penetrating or pointed shaft, such as a needle, is configured to pass through the guide cannula as well as the meniscus body or closely adjacent to the meniscus body. A line is connected to the penetrating shaft such that the line is drawn thereby through the guide cannula, the anatomical structure, and out from the skin layer. Thus, a pulling or kedging line is established.

A delivery cannula is also employed in the present apparatus. The delivery element may be formed as a delivery cannula having a relatively straight shaft or an angulated shaft. The delivery cannula includes a fixture to allow linkage to a connector on the line. In addition, the delivery cannula includes a compartment or space for holding the implant which is to be delivered across the tear of the anatomical structure. Linking of the line connector to the delivery cannula fixture allows the delivery cannula to be pulled or kedged by exerting a pulling force on the line. Consequently, the penetrating shaft and line are pulled, kedged, or towed across the anatomical structure and drawn outside the outer surface of the anatomical structure, such as the outside surface of the knee. Also, the implant delivery element is not drawn outside the knee.

It may be apparent that a novel useful apparatus for repairing a tear in an anatomical structure has been hereinabove described.

It is therefore an object of the present application to provide an apparatus intended for repairing a tear in an anatomical structure which is particularly useful in repairing meniscal tears in the knee.

Another object of the present application is to provide an apparatus for repairing a tear in an anatomical structure that utilizes a pulling force to position an implant across the tear rather than a pushing force found in the prior art.

Another object of the present application is to provide an apparatus for repairing a tear in an anatomical body that provides for positioning of a pulling line across the anatomical body and subsequently connects to an implant delivery device which is pulled to the site of the tear.

A further object of the present application is to provide an apparatus for repairing a tear in an anatomical body which is capable of repairing tears that, in the past, have been inaccessible with prior art devices.

Yet another object of the present application is to provide an apparatus for repairing a tear in an anatomical body that delivers an implant substantially perpendicularly to the axis or plane of the tear and subsequently permits a repair that is uniform and permanent.

Another object of the present application is to provide an apparatus for repairing a tear in an anatomical body that is relatively straightforward in use.

Another object of the present application is to provide an apparatus for repairing a tear in an anatomical body that can more accurately control the depth of an implant penetration and insertion in that anatomical body.

Another object of the present application is to provide a technique to more accurately control the depth of penetration of delivery instrument into an anatomic body by applying counter-traction to a pulled delivery instrument, thereby adjusting the net force of the delivery instrument.

Another object of the present application is to provide an apparatus and technique that can be utilized to repair tears of anatomic structures beyond those of the knee joint, for example, shoulder labral tears.

Another object of the present application is to provide an apparatus that advances a drill for an anatomic structure, such as a shoulder labral rim, and further advances a repair implant into a hole created by such drill.

Another object of the present application is to provide an apparatus for repairing a meniscal tear that is usable with prior art implantation instruments.

Another object of the present application is to provide an apparatus that places a repair implant across a meniscal tear by employment of a kedging line and eliminates the need for additional incisions in the human body.

Another object of the present application is to provide an apparatus for positioning a repair implant that employs a guide that precisely and predictably positions a kedging line for use in placing such implant.

Another object of the present application is to provide an all inside apparatus and technique or repairing a meniscal tear.

Another object of the present application is to provide an apparatus for improved repairing of a meniscal tear that results in an implant possessing improved alignment and accurate depth relative to the tear.

The application possesses other objects and advantages, especially as concerns particular characteristics and features thereof which will become apparent as the specification continues.

DETAILED DESCRIPTION OF THE SEVERAL VIEWS OF THE DRAWINGS

For a better understanding of the invention references made to the following detailed description of the preferred embodiments thereof which should be referenced to the prior described drawings.

DETAILED DESCRIPTION OF THE PREFERRED EMBODIMENTS

Various aspects of the present application will evolve from the following detailed description of the preferred embodiments thereof.

Figure 1:
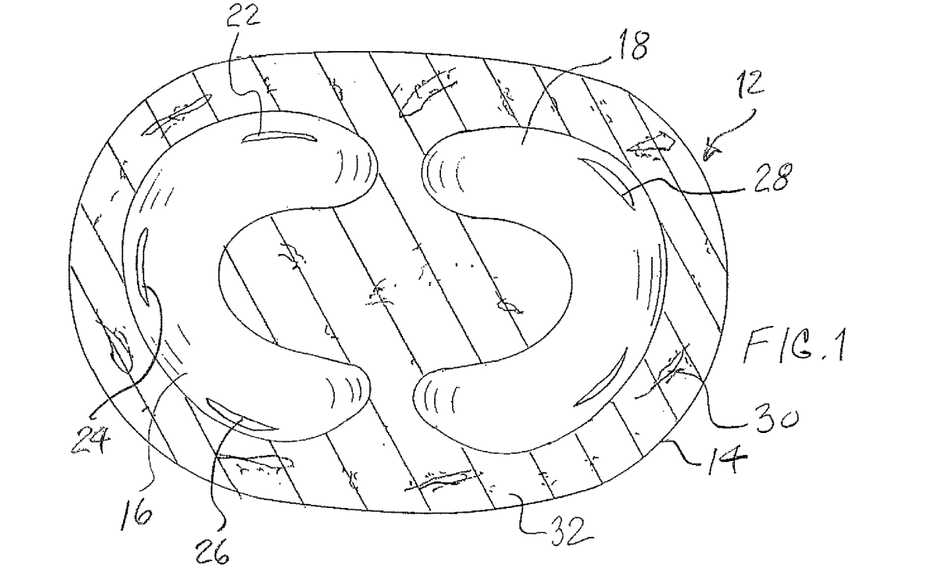
FIG. 1 is a sectional view of human knee depicting a pair of menisci having exemplary tears.

With respect to FIG. 1, it may be observed that a schematic view of a section of a human knee 12 is shown. Knee 12 includes a skin layer 14 and a pair of menisci 16 and 18. A plurality of representative meniscal tears 20 are also illustrated and are generally located in the peripheral third of each meniscus 16, 18. For example, meniscus 16 includes a posterior horn tear 22, a mid-body tear 24, and an anterior horn tear 26. Likewise, meniscus 18 exhibits a mid-body posterior tear 28 and an anterior mid-body tear 30. Again, the plurality of tears 20 exhibited in FIG. 1 are simply being employed as models for the following discussion of the novel apparatus of the present application. Portion 32 of knee 12 represents other anatomical structures within the knee such as bones, blood vessels, ligaments, and the like. Needless to say, knee 12 is represented in FIG. 2 and is oriented such that knee 12 includes an anterior portion 34 and a posterior portion 36.

Figure 2:
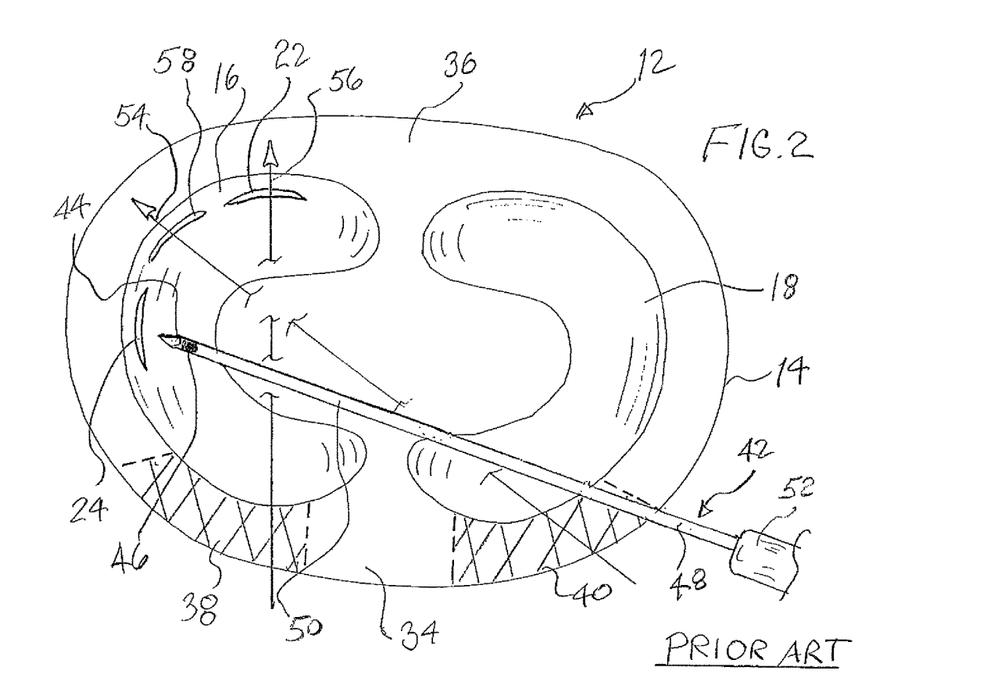
FIG. 2 is a top plan view of a pair of menisci in a human knee illustrating available portals of entry into the interior of the knee for effecting repair of meniscal tears.
Figure 3:
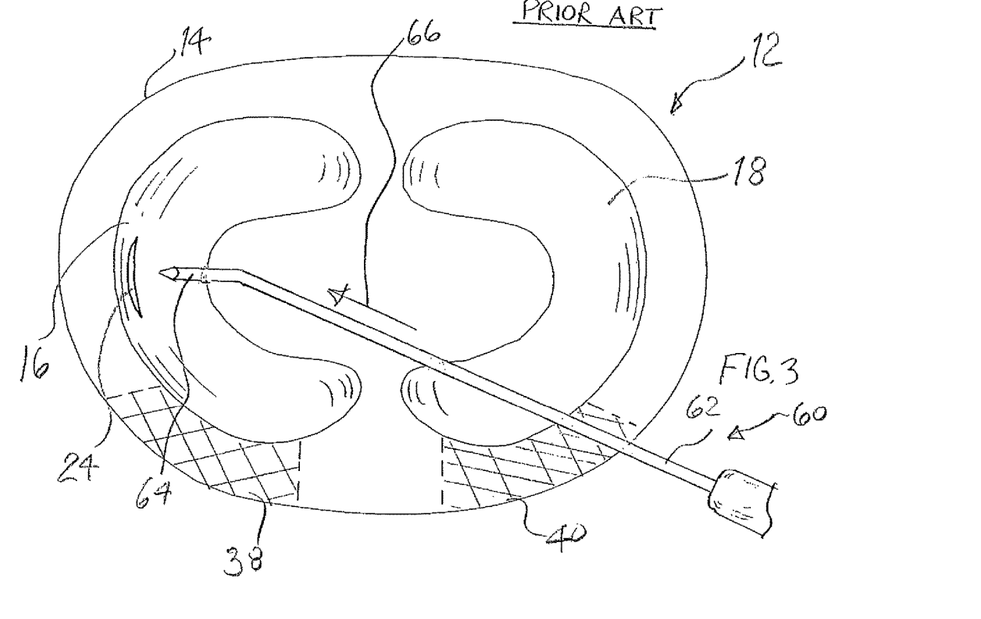
FIG. 3 is a top plan view of a delivery cannula utilizing a portal depicted in FIG. 2.
Figure 4:
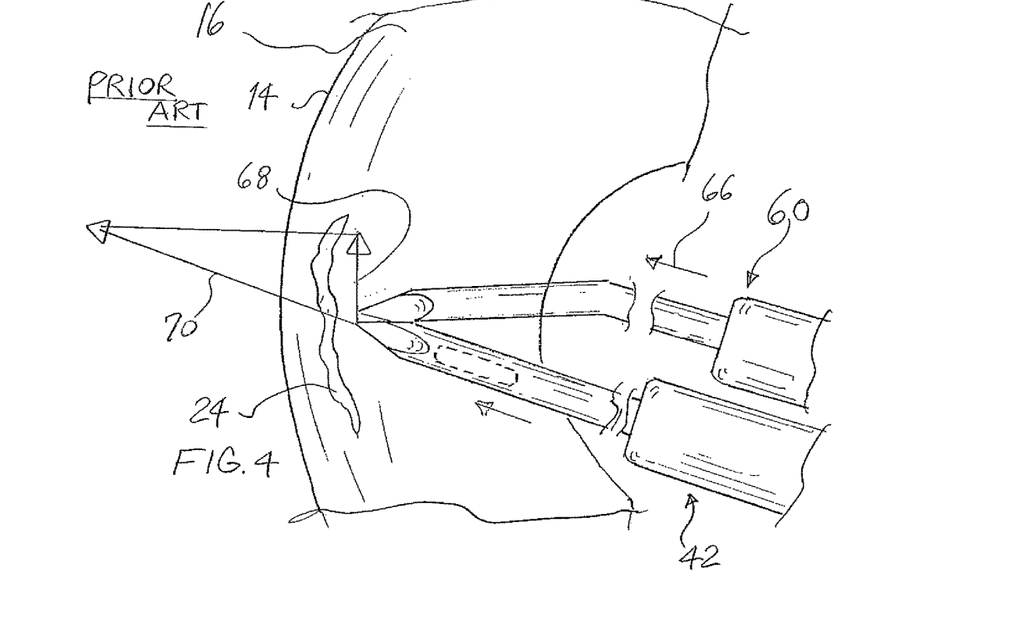
FIG. 4 is a top plan view showing the approach of a pair of delivery cannulas, partially illustrated, through a meniscal tear and the force vectors associated therewith.

Again, referencing FIG. 2, it may be observed that crosshatched areas 38 and 40 depict portals which are entry points for surgical instruments used to perform all-inside meniscal repairs. In other words, all other entry points along skin periphery 14 are precluded for surgical penetration because of anatomic obstructions or vulnerable structures within knee 12 which are a portion of schematically depicted anatomical structures 32 of FIG. 1. A prior art straight shaft repair device 42 is shown in FIG. 2 as passing through portal 40 and approaching tear 24 of meniscus 16. Repair device 42 includes a delivery shaft tip 44 housing a conventional repair implant 46 which may be in the form of a dart, clamp, anchor, suture, or similar known structures which are employed to repair meniscal tears. Repair device 42 also includes a delivery shaft 48 having a distal portion 50. Handle 52 is fixed to delivery shaft 48. Repair device 42 is representative of push motivated prior repair devices in the art of knee repair techniques. It should be noted that fixation implant 46 has been depicted in solid line for the sake of clarity in FIG. 2. Vectors 54 and 56 indicate that repair device 42 may be pushed through tears 58 and 22 perpendicular to the long edges of tears 58 and 22. Such a path of travel for repair device 42 would result in an optimal placement of fixation implant 46 across tears 58 and 22. However, the movement of repair device 42 across tear 24 results in an oblique alignment of repair device 42 with tear 24. The placement of fixation implant across tear 24 would ultimately result in an unacceptable buckling of the meniscal tear, since the delivery shaft tip 44 of repair device 42 does not enter the repair site of tear 24 at a perpendicular angle. With reference to FIG. 3, a repair device 60 is shown having a delivery shaft 60 with an angulated distal end 64. Again, repair device 60 is known in the art. Directional arrow 66 shows the direction of the force applied to repair device 42. Viewing now FIG. 4, it may be seen that the use of a prior art straight shaft repair device 42 or an angulated shaft repair device 60 still results in a shearing or lateral force across meniscus tear 24, represented by force arrow 68. Vector 70 represents the force exerted on straight shaft repair device 42 while vector 66 refers to the force applied by angulated repair device 60.

Figure 5:
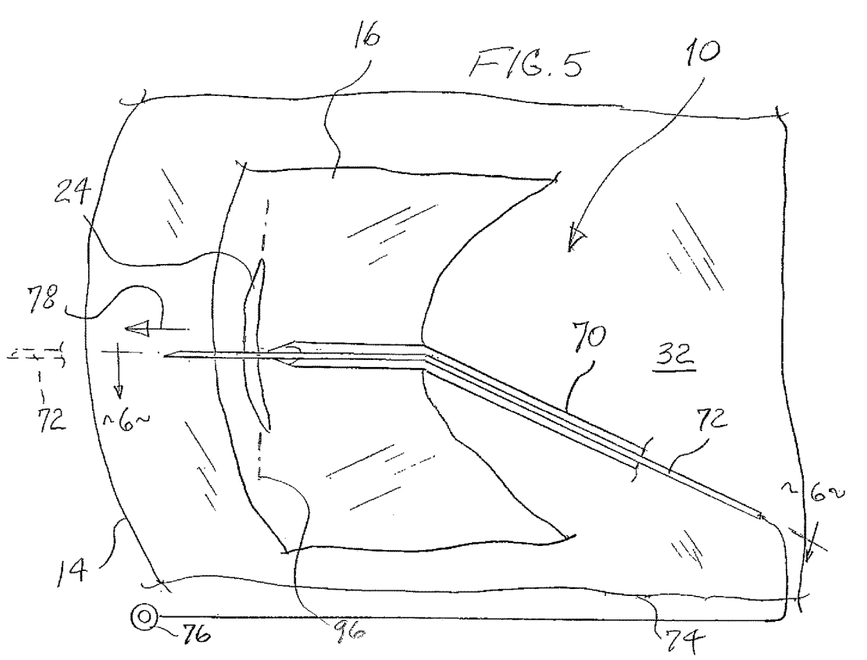
FIG. 5 is a top plan view of a portion of a meniscal tear in which the penetrating device of the present invention has been inserted across the meniscus.

Referring to FIG. 5, the apparatus 10 of the present application is illustrated in part. Apparatus 10 includes as one of its elements a guide which is in the form of a guide cannula 70. Guide 70 may also be fashioned as a chute, a rod, and the like. Guide cannula 70 may take the form of a straight cannula or an angulated cannula 70 as illustrated in FIG. 5. Also, a penetrating or pointed shaft or needle 72 is employed with guide cannula 70. Penetrating shaft 72 may take the form of a needle-like structure. Once guide cannula 70 is inserted into the knee structure through any of the portal zones 38 or 40, FIG. 2, penetrating shaft 72 is passed through guide cannula 70 and across tear 24 and through or closely adjacent to anatomical structure such as meniscus 16. Penetrating shaft 72 placement is usually accomplished by the practitioner utilizing an arthroscope to visualize the tear repair procedure. Since guide cannula 70 is used to control placement of penetrating shaft across tear 24, guide cannula is placed closely adjacent to and aligned perpendicularly to axis 96 of tear 24. As shown in FIG. 5, guide cannula 70 is angulated as necessary to establish the correct path for penetrating shaft 72 across tear 24. It should be realized that penetrating shaft may be formed of flexible materials such as nitinol and the like in order to be accommodated by angulated cannula 70. In certain cases, penetrating shaft 72 may be employed without guide cannula 70 for placement across tear 24.

Figure 6:
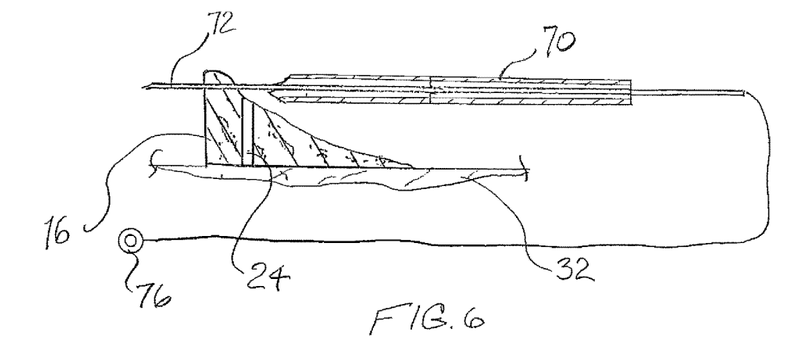
FIG. 6 is a sectional view taken along line 6-6 of FIG. 5.
Figure 7:
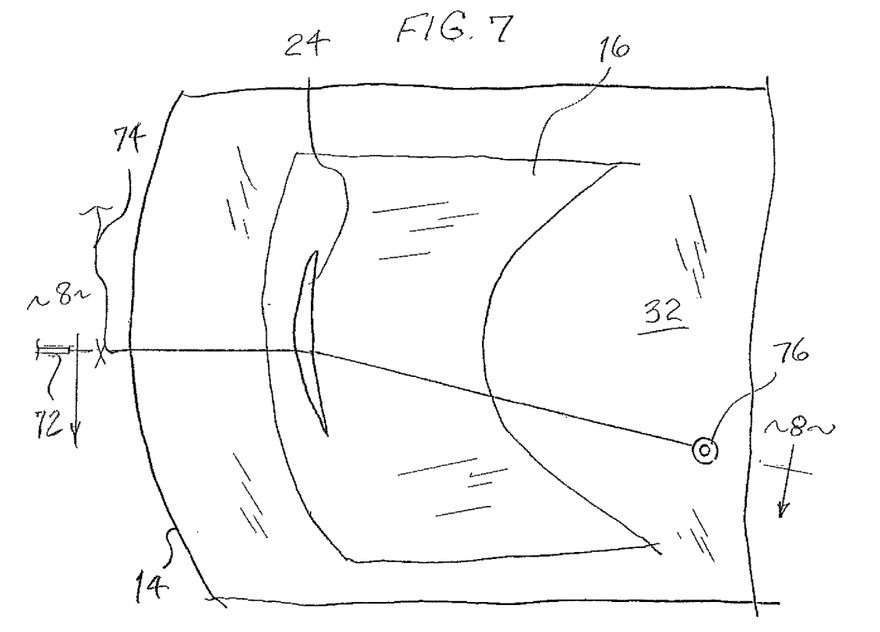
FIG. 7 is a top plan view of a portion of a meniscus showing the line of the present apparatus in place across a meniscal tear and in which the penetrating shaft has been severed from the line.
Figure 8:
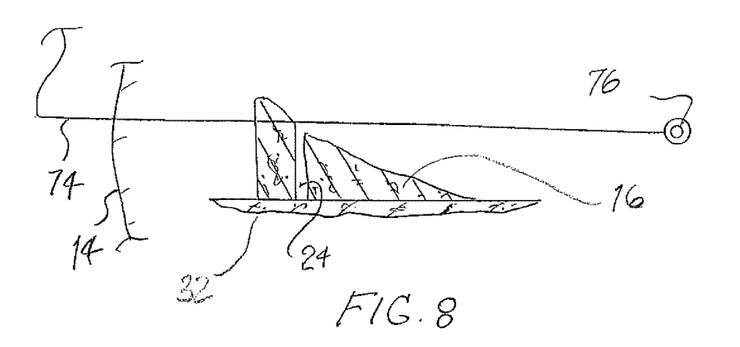
FIG. 8 is a sectional view taken along line 8-8 of FIG. 7.

A line 74, which may be formed of suture material, is connected to penetrating shaft 72. Line 74 may terminate in a connector 76 which is shown in FIGS. 5 and 6 as a ring. Connector 76 may also take the form of an end loop or a doubled over line forming a closed loop. Pointed or penetrating shaft 72 is then extended through skin layer 14 of the knee structure 12 partially shown in FIGS. 5 and 6. The movement of penetrating shaft 72 is represented by directional arrow 78. By this step, line 74 is also partially extended outside of the knee structure 12 beyond skin layer 14, FIGS. 7, 8, and 10. Penetrating shaft 72 is then severed from line 74. In other words, penetrating shaft 72 is advanced across tear 24 and outside knee joint 12 along with a portion of line 74. Thus, line 74 is established as a kedging, towing, or pulling line, and lies perpendicular to the axis 96 of tear 24.

Figure 9:
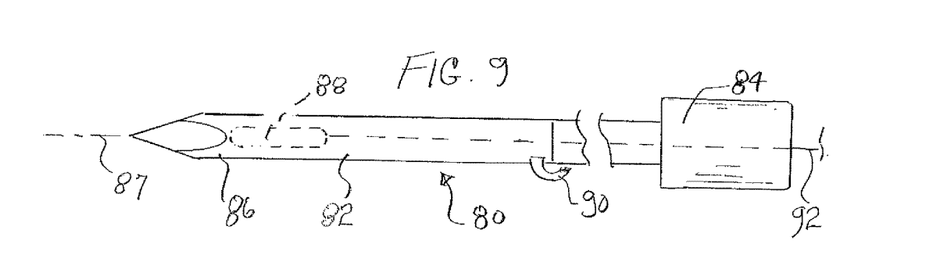
FIG. 9 is a broken partial top plan view of the delivery cannula of the present application.
Figure 10:
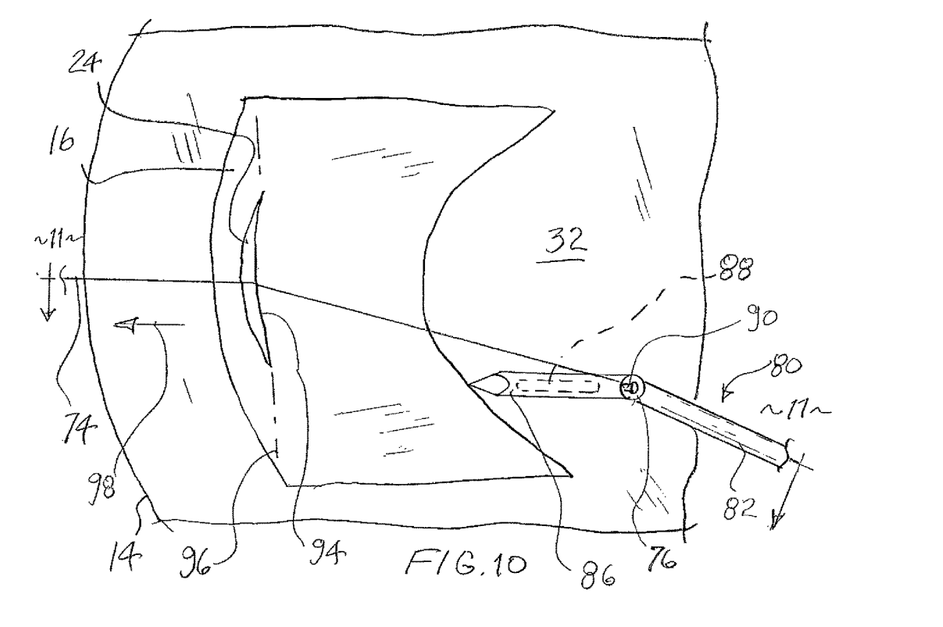
FIG. 10 is a top plan view of a partial meniscus indicating the line of the present application passing across the meniscal tear and connected to a delivery cannula.
Figure 11:
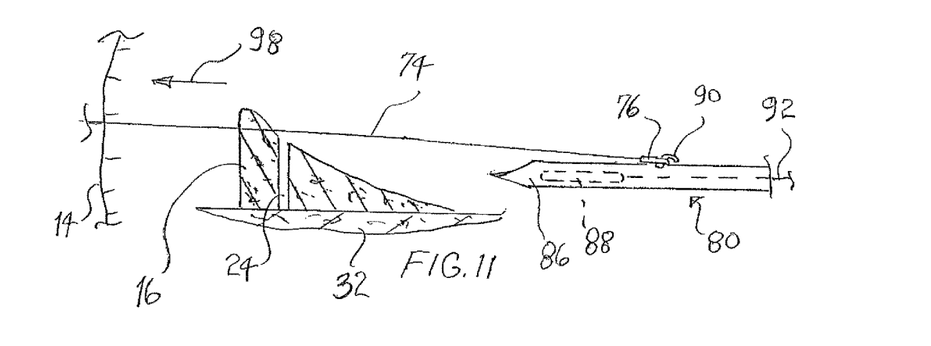
FIG. 11 is a sectional view taken along line 11-11 of FIG. 10.

With reference to FIGS. 9-11, it may be observed that apparatus 10 also includes a delivery element in the form of a delivery cannula 80. Delivery element 80 may also be fashioned as a chute, rod, or like structures. Delivery cannula 80 is shown as an angulated type. Delivery cannula 80 includes a delivery shaft 82 having a handle 84. Cannula 80 further is fashioned with a tip portion 86 which is capable of holding, in a space within cannula 80, a fixation implant 88 of known configuration, i.e. a dart, clamp, anchor, suture, and the like. Moreover, delivery cannula 80 is also provided with a fixture 90 which may be in the form of a cleat. It should be apparent that connector ring 76 of line 74 engages cleat 90 to allow kedging, pulling or towing of delivery cannula 80. In certain instances, line 74 may terminate in a bead that engages a slot on delivery cannula 80 to allow the pulling of delivery cannula 80 by line 74. Further, line 74 may be linked directly to implant 88 without the use of delivery cannula 80. Moreover, a deployment mechanism 92, of conventional configuration, serves as a directing mechanism for fixation of implant 88 within deployment cannula 80. It should be noted that line 74 delivered by penetrating shaft 72 has passed across meniscal tear 24 generally perpendicularly to the edge 94 thereof. In general, line 74 lies essentially perpendicular to axis 96. Kedger line 74 is then pulled according to directional arrow 98 from outside the knee structure 14. A counter traction may be applied to delivery cannula 80 to adjust the net force on delivery cannula 80 resulting from the pulling of line 74 and the traction exerted on delivery cannula 80. At this point, delivery cannula 80 is introduced into the knee joint 12. Line 74 is further pulled until the tip 86 of delivery cannula 80 lies at tear 24. The desired delivery cannula 80 alignment with tear is then confirmed. If axis 87 of tip is not perpendicular to axis 96 of tear 24, tip 86 is angulated to correct alignment. Such angulation of delivery cannula 80 may be achieved prior to insertion into knee 12. If guide cannula 70 was angulated to establish correct alignment with axis 96 of tear 24, guide cannula 70 can be used as template for angulation of delivery cannula tip 87 before insertion into joint 12. It should be noted that the position of tip 86 determines the access to tear 24 independently of the position of handle 84. Where a delivery cannula is not employed, implant 88 is pulled into place directly by line 74.

Figure 12:
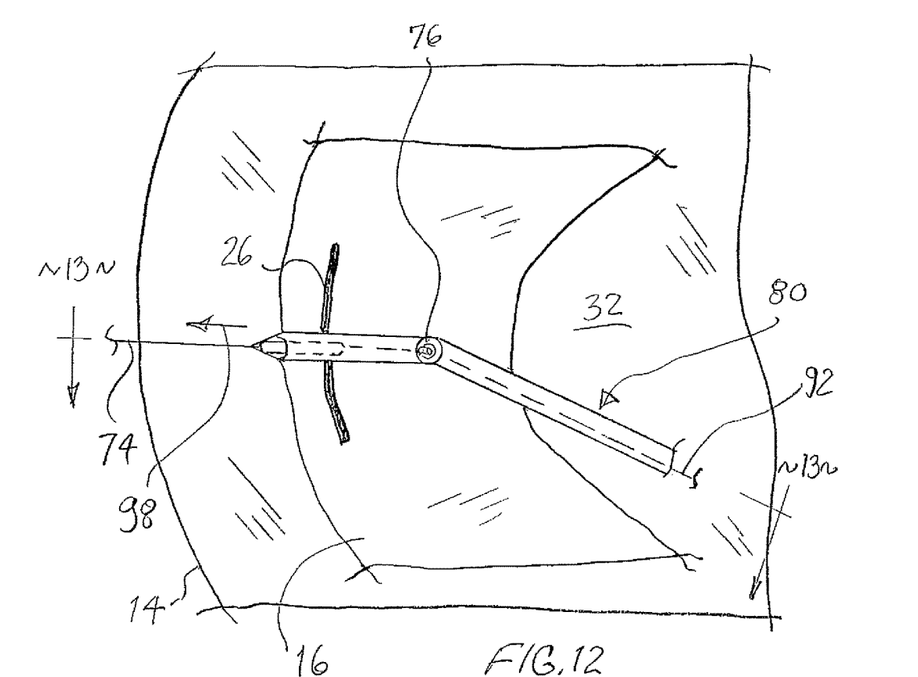
FIG. 12 is a top plan view showing a partial meniscus with an implant cannula passing across a meniscal tear prior to delivery of an implant.
Figure 13:
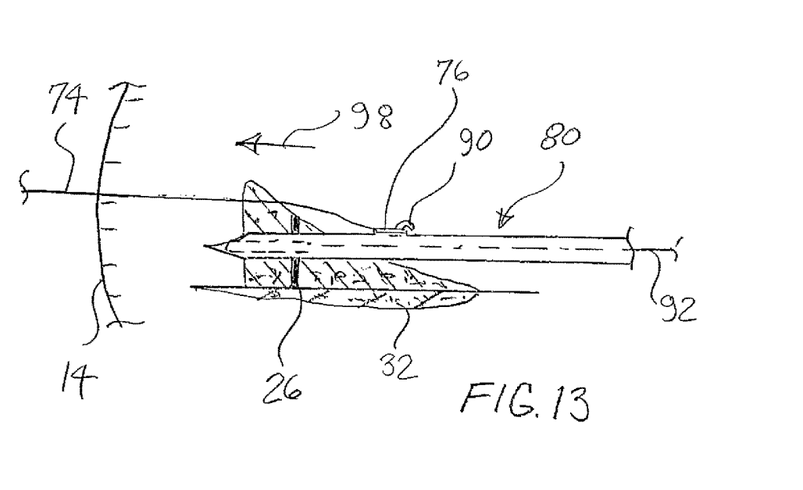
FIG. 13 is a sectional view taken along line 13-13 of FIG. 12.

Thus, the anterior areas of meniscus 16, not reachable by prior art references, are now accessible by apparatus 10. At this point, delivery cannula 80 has advanced into knee joint 12, positioned at tear 26, and pulled by kedging or towing line 74 directly across tear 26. FIGS. 12 and 13 represent such movement of delivery cannula 80. The depth of insertion of delivery cannulas is controlled by the pull of line 74. Again, delivery cannula 80 can be restrained to provide counter-traction to the pull of line 74 to calibrate the net pulling force of line 74 and prevent inadvertent over penetration of delivery cannula tip 87. In certain embodiments, guide cannula 70 may be joined to delivery cannula to establish correct placement of penetrating shaft 72 and line 74.

Figure 14:
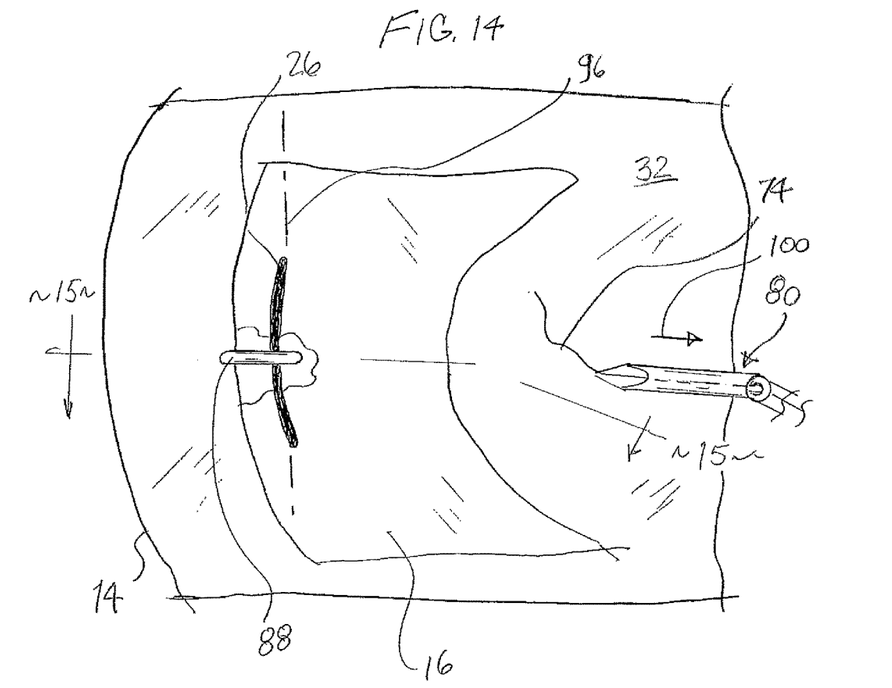
FIG. 14 is a top plan view showing a partial meniscus with an implant having been delivered across a meniscal tear by the apparatus of the present application.
Figure 15:
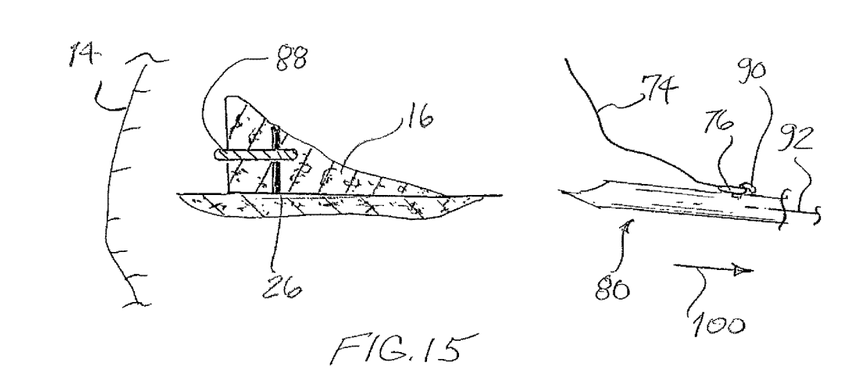
FIG. 15 is a sectional view taken along line 15-15 of FIG. 14.

At this point, fixation implant 88 is deployed by mechanism 92 from delivery cannula 80. Once deployed, FIGS. 14 and 15, delivery cannula 80 and line 74 are removed or retracted from tear 26, directional arrow 100. It should be realized that fixation implant 88 now lies directly across tear 26 and substantially perpendicular to axis 96, which provides a superior alignment of fixation implant with tear 26. Such positioning of implant 88 avoids the buckling of tear 26 resulting from push-type repair devices of the prior art. Needless to say, such prior art buckling resulted from fixation implant 88 being pushed across tear 26 at an oblique angle relative to the axis 96 or the edges of tear 26.

While in the forgoing embodiments of the present invention have been set forth in considerable detail for the purposes of making a complete disclosure of the invention, it may be apparent to those of skill of the art that numerous changes may be made without departing from the spirit and principles of the invention.

What is claimed is:

1. An apparatus for repairing a tear in an anatomical structure of a human body utilizing an implant, comprising:
    a guide component capable of insertion into the human body proximate the anatomical structure;
    a penetrating shaft being configured to pass through the guide component, the penetrating shaft capable of delivering a line through and extending beyond the human body proximate the anatomical structure;
    the line, capable of being connected to a delivery component, the line further capable of being pulled so as to move the delivery component from a first location in the human body to a second location in the human body proximate the anatomical structure; and
    the delivery component comprising a space for holding the implant, the implant capable of being implanted to repair the tear in the anatomical structure.

2. The apparatus of claim 1 in which the guide component comprises a guide cannula.

3. The apparatus of claim 1 in which the delivery component comprises a delivery cannula.

4. The apparatus of claim 1 in which the delivery component further comprises a handle.

5. The apparatus of claim 1 in which the penetrating shaft comprises a needle.

6. The apparatus of claim 2 in which the guide cannula comprises an angulated member.

7. The apparatus of claim 3 in which the delivery cannula comprises an angulated member.

8. The apparatus of claim 3 in which the delivery cannula further comprises a handle.

9. The apparatus of claim 3 in which the line further comprises a connector being configured to engage a delivery cannula fixture component.

10. The apparatus of claim 9 in which the delivery component further comprises a handle.

11. The apparatus of claim 9 in which the guide component further comprises an angulated member.

12. The apparatus of claim 11 in which the delivery component further comprises an angulated member.

13. The apparatus of claim 11 in which the delivery component further comprises a handle.

14. An apparatus for repairing a tear in an anatomical structure of a human body, comprising:
    a penetrating shaft being configured to pass through a guide component and the anatomical structure; and
    a line being connected to the penetrating shaft, the line being configured to pass through and extending beyond the human body proximate the anatomical structure, the line capable of being connected to a delivery component, the line further capable of being pulled so as to move the delivery component from a first location in the human body to a second location in the human body proximate the anatomical structure for repairing the tear.

15. The apparatus of claim 14 in which the delivery component comprises: a fixture component for linkage to the line, the delivery component-further including a space for holding an implant.

16. The apparatus of claim 14 in which the penetrating shaft comprises a needle.

17. The apparatus of claim 14 in which the guide component comprises a guide cannula.

18. The apparatus of claim 14 in which the guide component further comprises a handle.

19. The apparatus of claim 14 in which the guide component further comprises an angulated member.

* * * * *